United States Patent [19]

Blackwood

[11] Patent Number: 5,243,185
[45] Date of Patent: Sep. 7, 1993

[54] APPARATUS AND METHOD FOR ICE DETECTION

[75] Inventor: Carl I. R. Blackwood, Campbell, Calif.

[73] Assignee: Loral Aerospace Corp., New York, N.Y.

[21] Appl. No.: 922,873

[22] Filed: Jul. 31, 1992

[51] Int. Cl.$^5$ ............................................. G02F 1/01
[52] U.S. Cl. .................................... 250/225; 340/583
[58] Field of Search ................... 250/225, 231.13, 342, 250/338.1, 352; 356/369, 367, 336, 338; 340/580, 581, 582, 583, 962, 602

[56] References Cited

U.S. PATENT DOCUMENTS

| | | | |
|---|---|---|---|
| 4,327,286 | 4/1982 | Thoma | 340/583 |
| 4,668,860 | 5/1987 | Anthon | 250/225 |
| 4,701,052 | 10/1987 | Schoen | 356/369 |
| 4,725,145 | 2/1988 | Azzam | 356/367 |
| 5,170,049 | 12/1992 | De Jonge et al. | 250/225 |

*Primary Examiner*—David C. Nelms
*Assistant Examiner*—Que T. Le
*Attorney, Agent, or Firm*—Edward J. Radlo; Greg T. Sueoka

[57] ABSTRACT

An apparatus and method that accurately and reliably detects ice on a target surface (20). Intrinsic birefringent properties of hexagonal ice crystals are used to detect ice by analyzing elliptically-polarized reflection of linearly-polarized radiation from ice. A linearly-polarized radiation beam (15) is focused on the target surface (20), and returned radiation (25) is filtered (30) as a function of its elliptical polarization. Filtered radiation (35) is directed to a sensor (40) and quantified according to the intensity of radiation received at various points ($41_1$–$41_n$) on the filter (30), and an output signal for each point is produced ($45_1$–$45_n$). The presence or formation of ice is determined by a signal processor (50) that detects the variance among the output signals ($45_1$–$45_n$)—a variance (55) reaching a threshold value being indicative of ice. Filtering unit (30) may be composed of two polarizing filters (31 and 33), rotatable with respect to each other on a common axis and disposed in a parallel plane therewith. A reading is taken from all the output signals ($45_1$–$45_n$), and an output signal variance (55) is calculated. The filters (31 and 33) are then rotated with respect to each other (e.g., several degrees), another reading is taken, and another variance (55) is calculated. This read-calculate-rotate cycle is repeated continuously. Thus, this embodiment is more accurate since it relies on a greater number of samples, and such samples are taken over numerous time periods. Also, because the output from the filter (33) is dynamically changing as the two filters (31 and 33) are rotated, the presence of ice is easier to detect visually.

9 Claims, 5 Drawing Sheets

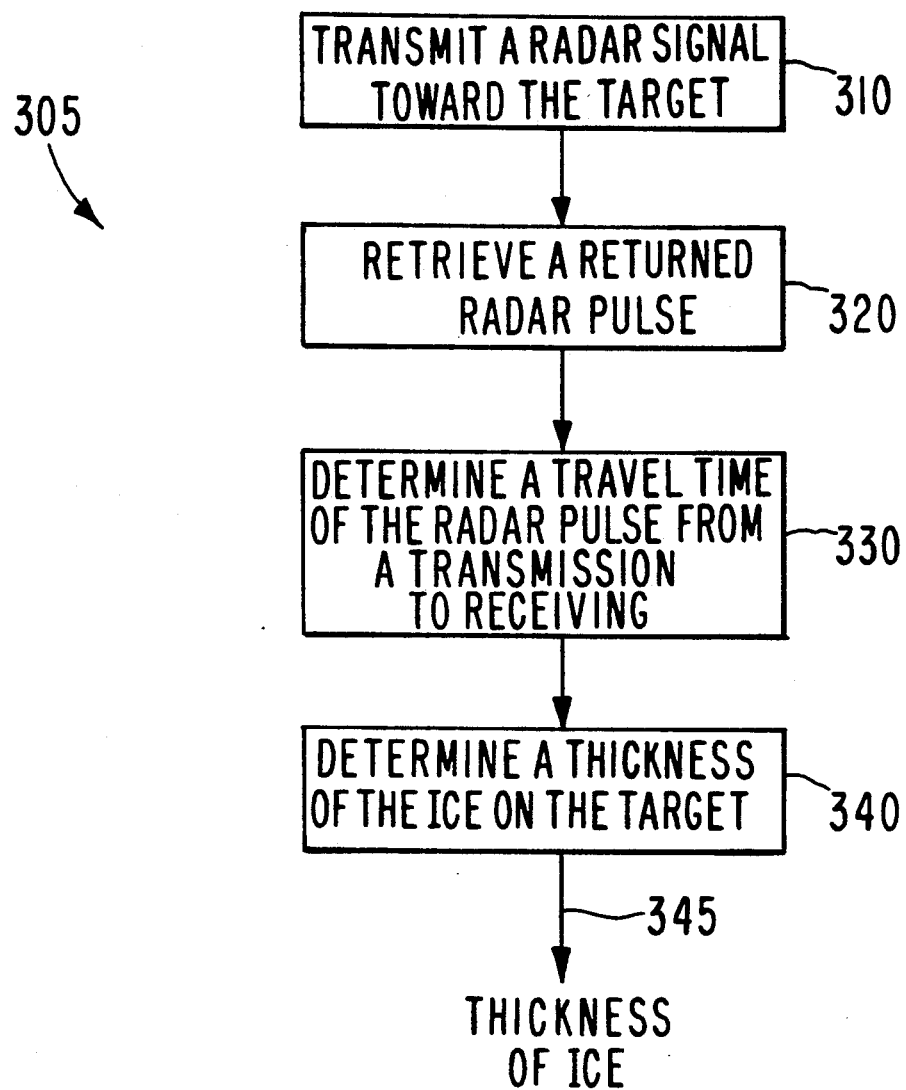

APPARATUS AND METHOD FOR ICE DETECTION

TECHNICAL FIELD

This invention involves the detection of ice on a remote surface using optical components and a variance analysis.

BACKGROUND ART

U.S. Pat. No. 4,701,052 (Schoen) discloses a dew point hygrometer that uses linearly-polarized light to detect condensate on a metal surface. Schoen declares the presence of condensation when a light detector receives no light from an analyzer.

U.S. Pat. No. 4,725,145 (Azzam) discloses a polarimeter from which one parameter of polarization of a light beam can be determined. The Azzam invention is a polarization sensitive photodetector that produces an output proportional to the radiation absorbed by the photodetector.

U.S. Pat. No. 4,668,860 (Anthon) discloses a scattermeter for evaluating the surface quality of an optical element, wherein surface scatter is distinguished from bulk scatter by differing polarization characteristics. Neither Azzam nor Anthon incorporate the intrinsic birefringent properties of the hexagonal crystalline structure of the ice crystal.

Limitations of the prior art reveal the need for an accurate and reliable ice detection system. The present invention uses the intrinsic birefringent properties of the hexagonal ice crystal to detect ice by analyzing the elliptically-polarized reflection of linearly-polarized radiation on ice using a plurality of elemental sensors—the determination of ice being a function of the variance among the output signals of the sensors. The ice detection system of the present invention is advantageous over the prior art because it provides more information through a qualitative measurement, and is more accurate because it is based on multiple inputs.

DISCLOSURE OF INVENTION

The present invention is an apparatus (5) and a method (205) for detecting the presence of formation of ice by directing a linearly-polarized radiation beam (15) on a target area (20), filtering (30) the returned radiation (25) as a function of the degree of elliptical polarization, producing output signals ($45_1$–$45_n$) as a function of the amount of radiation passed through the filter (30), and determining the variance among the output signals—a variance reaching a threshold value being indicative of ice (55). Since multiple output signals ($45_1$–$45_n$) are analyzed to determine the presence of ice, the measurement is more accurate than a single-output signal sampling. Also, a qualitative variance measurement provides additional information to the "ice" or "no ice" determination.

Transmitter (10) is used to generate linearly-polarized radiation (15) which is directed toward a target (20). The birefringent property (described below) of the polycrystalline hexagonal structure of ice causes the incident radiation (15) to be polarized elliptically upon return (25). The orientation of each ice crystal with respect to some reference axis determines the degree of elliptical polarization of the incident radiation.

The returned radiation (25) is filtered (30) as a function of its elliptical polarization. The amount of filtered radiation (35) passing through the filter (30) is detected by a sensor (40) which comprises an array of elemental radiation-detection sensors ($41_1$–$41_n$), preferably CCD (charge-coupled device) cells. Each elemental sensor produces an output signal ($45_1$–$45_n$) that is a function of the amount of radiation received. To determine the presence or formation of ice on the target surface (20), a signal processor (50) calculates the variance (55) among the output signals ($45_1$–$45_n$). Because ice crystals are oriented randomly, a high variance is symptomatic of ice crystals present on the surface. It is important to note that it is the variance in output, not the amount of output, that indicates the presence or formation of ice.

One embodiment of the filtering unit (30) uses two polarizing filters (31 and 33) to filter returned radiation (25). A first filter (31) filters the returned radiation (25) as a function of the elliptical polarization, resulting in semi-filtered radiation (32). A second filter (33) is rotatable with respect to the first filter (31) on a common axis and disposed in a parallel plane therewith. The second filter (33) filters the semi-filtered radiation as a function of the elliptical polarization, resulting in filtered radiation (35). As described above, a reading is taken from all the output signals ($45_1$–$45_n$), and an output signal variance is calculated. The filters (31 and 33) are then rotated with respect to each other (e.g., several degrees), another reading is taken, and another variance is calculated. This read-calculate-rotate cycle is repeated continuously. This embodiment is more accurate since it relies on a greater number of sample readings, and such readings are taken at different time periods. Also, because the output from the filter (33) is dynamically changing as the two filters are rotated, the presence of ice is easier to detect visually.

After the presence of ice is determined, a thickness of the ice is determined (505). A short-pulse radar signal (515) is transmitted toward the target (20). A receiver (530) receives the returned pulse (525), and a radar signal processor (540) determines the thickness of the ice (545). The thickness is a function of the travel time (t) of the pulse from sending to receiving, an ice-to-air interface dielectric discontinuity, an ice-to-surface interface dielectric discontinuity, and a dielectric constant in the ice. The thickness, $T_i$, is computed from: $T_i = 14.99 \, t/(E_{ice})^{\frac{1}{2}}$, where $E_{ice}$ is the dielectric constant of the ice.

BRIEF DESCRIPTION OF THE DRAWINGS

FIG. 8 illustrates a flowchart of a method for determining the thickness of ice.

DETAILED DESCRIPTION OF THE PREFERRED EMBODIMENTS

The present invention discloses an apparatus and method for detecting ice on a surface accurately and reliably. The invention is useful for detecting ice formation on aircraft wings and other areas of the fuselage where ice deposits may compromise the aerodynamic integrity of the airborne system. Other applications include: detection of ice patches on roads to provide safer travel; detection of ice formation inside engines to warn of engine failure; and, monitoring equipment which function in environments where ice is likely to form.

Figure 1A:
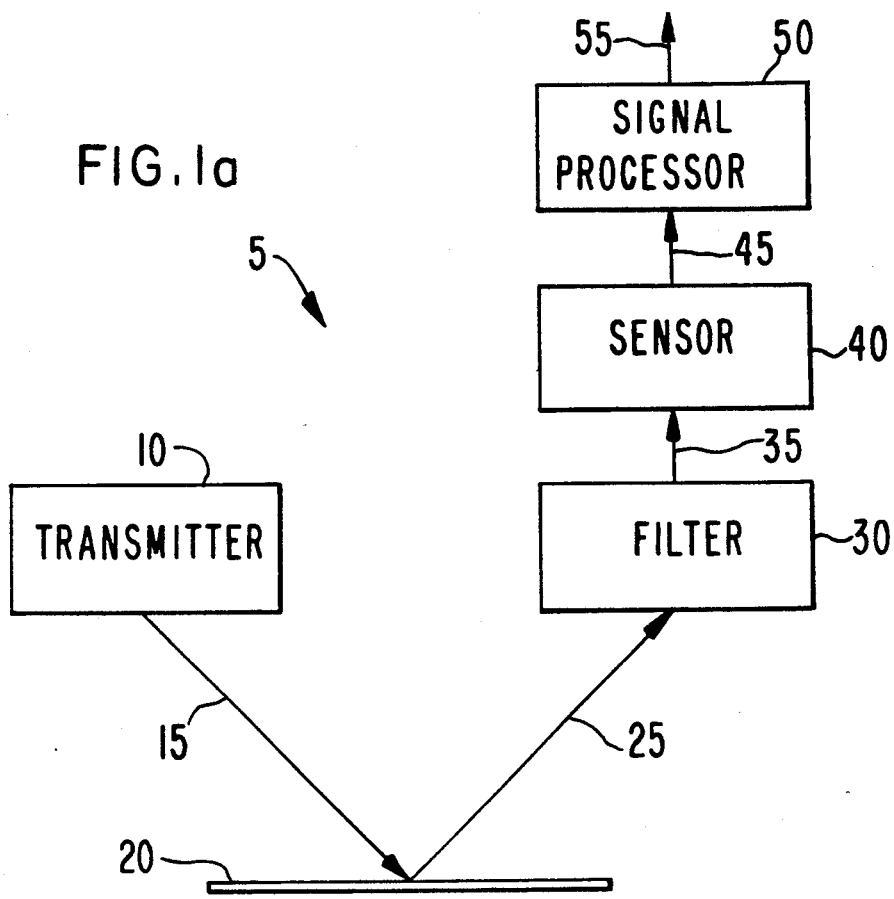
FIG. 1a illustrates the main components of the present invention for ice detection.

FIG. 1a illustrates the main components of an ice detection apparatus that comprises: transmitter 10; target surface 20; filter 30; sensor 40; and, signal processor 50.

The transmitter 10 generates linearly-polarized radiation 15 (e.g., linearly-polarized light). Linearly-polarized light can be produced by passing unfiltered light through a linearly-polarized filter. It is also conceivable to use a low-power semiconductor laser (e.g., operating in the 2-5 mW range, and equipped with a Brewster window polarizing filter) to produce linearly-polarized radiation.

Figure 1B:
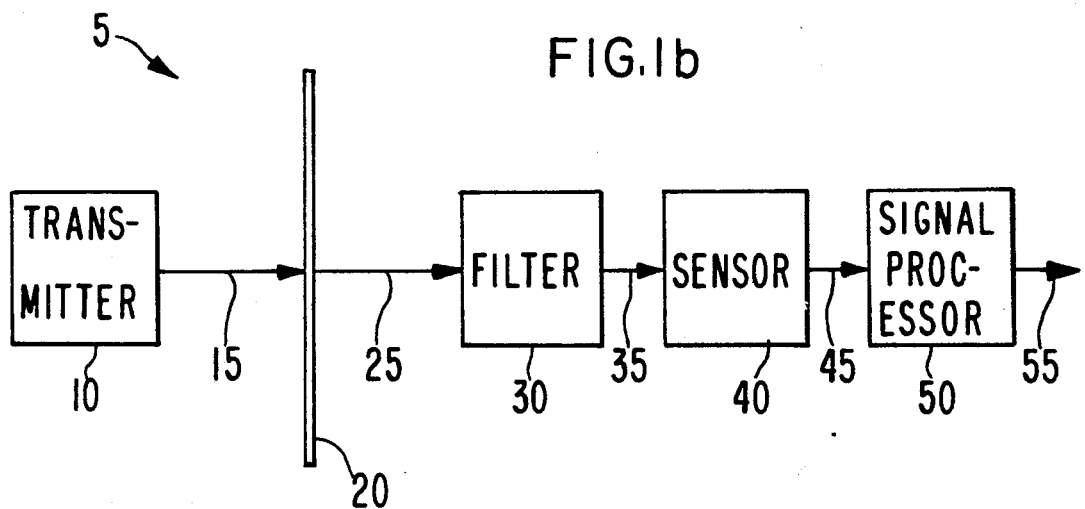
FIG. 1b illustrates the invention configured for linearly-polarized radiation refracting through a target surface.

The linearly-polarized radiation 15 is directed toward the target 20. The linearly-polarized radiation 15 is returned 25 from the target 20 by either reflection from (FIG. 1a) or refraction through (FIG. 1b) the target 20. If the returned radiation 25 is reflected, the filter 30 is located on the same side of the target surface 20 as the transmitter 10 as in FIG. 1a. If the returned radiation 25 is refracted through the target 20 (e.g., the target is translucent), the filter 30 can be located on an opposite side of the target surface 20 from the transmitter 10, as in FIG. 1b.

Figure 2A:
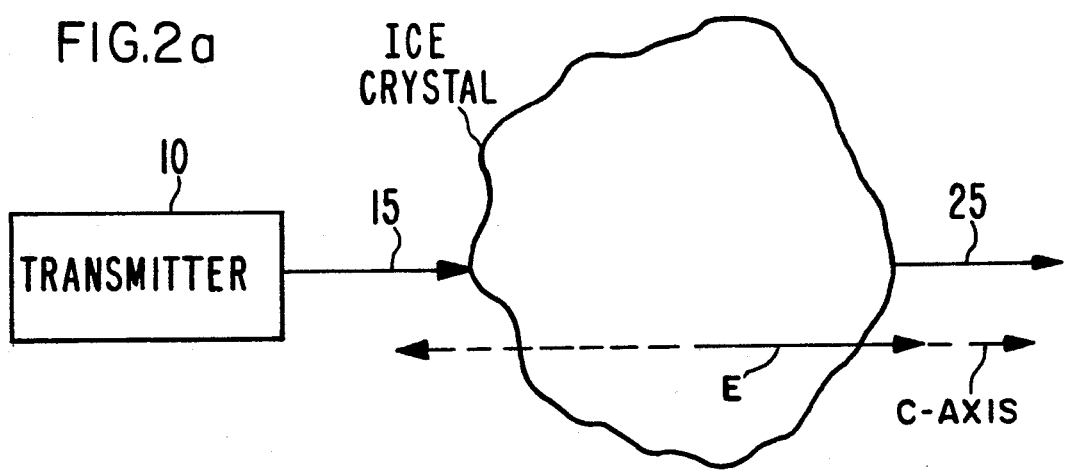
FIG. 2a illustrates linearly-polarized radiation incident parallel to the c-axis of an ice crystal.
Figure 2B:
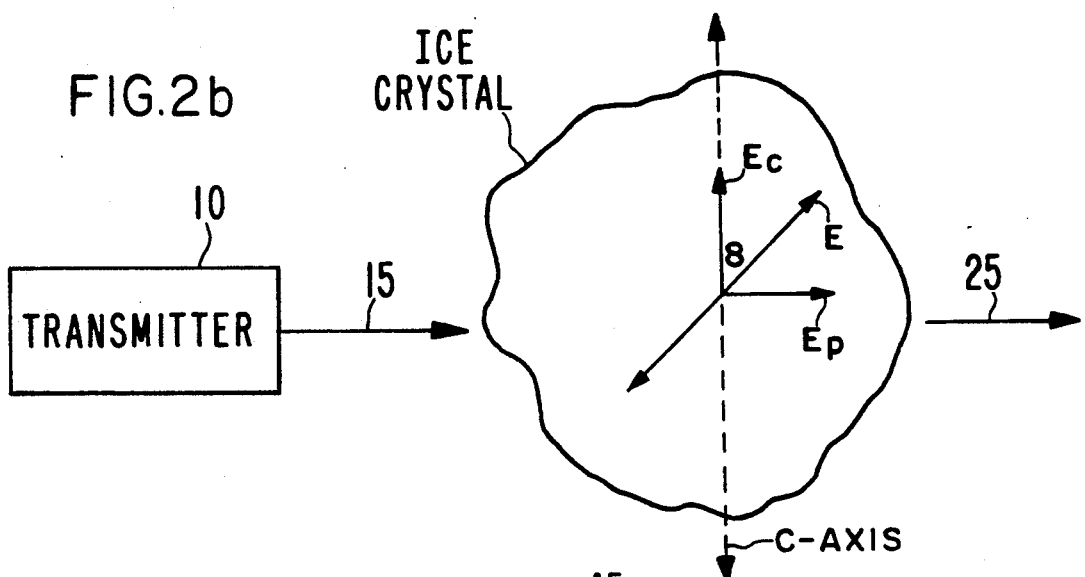
FIG. 2b illustrates linearly-polarized radiation incident perpendicular to the c-axis of an ice crystal.

The birefringent property of the hexagonal crystalline structure of ice causes the incident linearly-polarized radiation 15 to become elliptically-polarized radiation 25 upon return (via either reflection or refraction). Optically, ice is a uniaxial crystal, with the optic axis being the c-axis of crystallographic notation. If linearly-polarized radiation 15 is incident parallel to the c-axis of the ice crystal, the returned radiation's 25 direction of polarization, defined by the electric vector E, is unaltered. Thus, linearly-polarized radiation 25 is returned from the ice crystal as shown in FIG. 2a. If linearly-polarized radiation 15 is incident perpendicular to the c-axis of the ice crystal, then E is altered such that there is an angle $\theta$ between E and the c-axis of the crystal as shown in FIG. 2b. The returned radiation 25 is separated into "ordinary" and "extraordinary" rays that travel at different speeds in the ice crystal, and are refracted at different angles. In this instance, the electric vector of returned radiation 25, E, can be resolved into components, $E_c$, parallel to the c-axis, and $E_p$ perpendicular to it. The component, $E_p$, is the ordinary ray, and $E_c$ is the extraordinary ray. Before entering the ice crystal, ray components $E_c$ and $E_p$ are in phase. After traveling through the ice crystal at different speeds, $E_c$ and $E_p$ are out of phase (unless the thickness of the ice crystal causes a phase difference that is an integer multiple of $2\pi$). The phase difference between the two rays $E_c$ and $E_p$ will depend on the thickness of the crystal. Combined, $E_c$ and $E_p$ produce elliptically-polarized radiation 25. The degree of polarization varies with the phase difference between $E_c$ and $E_p$ (and thus the thickness of the ice crystal). If the incidence of linearly-polarized radiation 15 is neither parallel nor perpendicular to the c-axis of the ice crystal, the velocity of the extraordinary component, $E_c$, varies with the angle of incidence with the c-axis. Because of the randomness of the various c-axes of the ice crystals with respect to the incident linearly-polarized radiation 15, some of the refracted rays of radiation 25 will be more elliptically polarized than others.

The filter 30 is disposed in the path of the returned radiation 25. The filter 30 allows to pass the component of the returned radiation 25 that is polarized parallel to the preferred direction of the filter, $E_c$; and rejects the component of the returned radiation 25 that is polarized perpendicular to the preferred direction of the filter, $E_p$. Thus, the filter 30 outputs filtered radiation 35 that is a function of the elliptical polarization of the returned radiation 25. A blocking filter for screening ambient, non-signal bearing, circularly polarized, or plane polarized radiation may improve the signal-to-noise ratio at the filter 30. Also, after gathering deterministic responses from viewing the target 20 at different viewing distances, there may be a need to refocus the image by shifting the plane of the filter 30 further from the target 20 since the target surface may be too close to assume parallel incidence.

Figure 3:
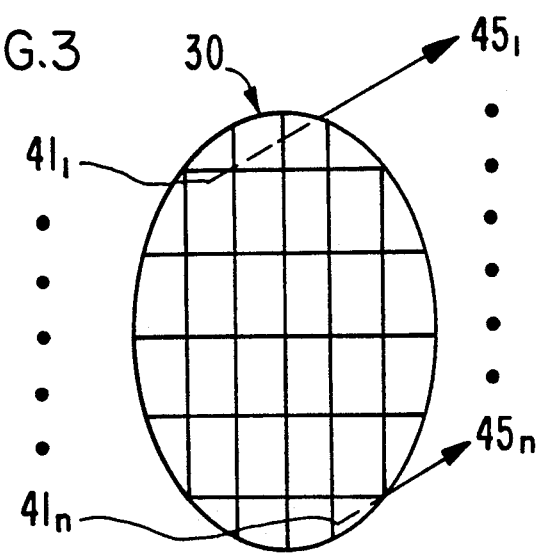
FIG. 3 illustrates placement of an array of elemental sensors on a filter.

A sensor 40 is disposed in the path of the filtered radiation 35 and detects the amount of filtered radiation 35 passing through filter 30. Sensor 40 is comprised of an array of elemental radiation-detection sensors $41_1$–$41_n$ (preferably CCD cells). The elemental sensors $41_1$–$41_n$ are placed uniformly on an output side of the filter 30 (or in a plane parallel with the plane of the filter 30) such that they receive the filtered radiation output from the filter 30 as shown in FIG. 3. The number of elemental sensors $41_1$–$41_n$ is determined by the resolution sought. Each elemental sensor produces an output signal $45_1$–$45_n$ that is a function of the amount of radiation received at that location. The output signal may be in the form of a voltage potential, analog or digital signal, optical intensity, or other suitable indication.

The output signals $45_1$–$45_n$ of the elemental sensors $41_1$–$41_n$ are connected to a signal processor 50. The signal processor 50 may be comprised of any standard electrical voltage potential measuring components, a digital computer, or other suitable measuring and logic devices. The signal processor 50 determines a variance 55 among the output signals. The mathematical interpretation of variance is used in this context (e.g., the square of the standard deviation of a sequence of numbers). For a "no ice" condition, the variance 55 is zero (or close to zero); and, for an "ice" condition, the variance 55 is greater than zero. The "ice" or "no ice" threshold value may be determined using statistical results. Also, controlled empirical studies in which the ice-free surface is "viewed" can be made to determine that the surface is optically neutral. Such an observation would yield a deterministic response of the ice detection apparatus for that surface in an ice-free environment. This datum would be useful for establishing a reference base-variance against which the ensuing field variances could be compared. Thus, the number of "false alarm" indications of ice formation may be reduced. It should be noted that the randomness of the variations in output signals of contiguous elemental sensors is the operative feature since the existence of no ice could also be marked by gradual variations in output signals across contiguous elemental sensors. Among other uses, the output of the signal processor 55 (the variance among the output signals $45_1$–$45_n$ and a determination of "ice" or "no ice") can be stored in a memory means for reference, visually displayed, or used to change the state of an instrument or device.

Figure 4:
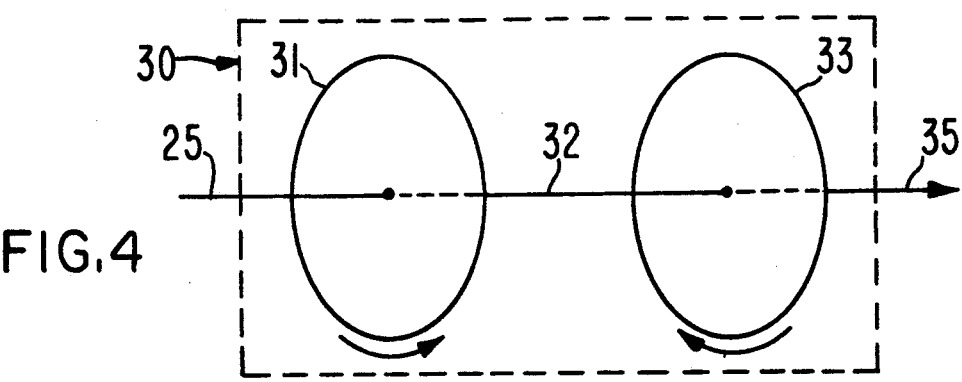
FIG. 4 illustrates one embodiment of a filter using two linearly-polarized filters.

FIG. 4 shows one embodiment of the invention where filter 30 comprises two polarizing filters 31 and 33, rotatable with respect to each other on a common axis and in a parallel plane therewith. The first filter 31 filters the returned radiation 25 as a function of the elliptical polarization as described above, resulting in semi-filtered radiation 32. The second filter 33 filters the semi-filtered radiation as a function of the elliptical polarization as described above, resulting in filtered radiation 35. The analysis for determining the presence or absence of ice relies on reading the output from each of the elemental sensors $45_1$–$45_n$ for every D degrees of arc of rotation of the filters with respect to each other (e.g., where D=2°). The rate at which the filter is rotated is dependent only on the sample rate that can be achieved by the signal processor 50. At each discrete rotation position, the signal processor 50 calculates the variance 55 of the output signals $45_1$–$45_n$. The filters 31 and 33 are then rotated with respect to each other (e.g., resulting in several degrees relative offset), and a reading from the array of elemental sensor output signals $45_1$–$45_n$ is repeated, such that another variance may be calculated. This read-calculate-rotate process is repeated numerous times. This embodiment is more accurate since it relies on a greater number of samples, and such samples are taken at different time periods. Also, because the output from the filter 33 is dynamically changing as the two filters are rotated, the presence of ice is easier to detect visually.

Figure 5:
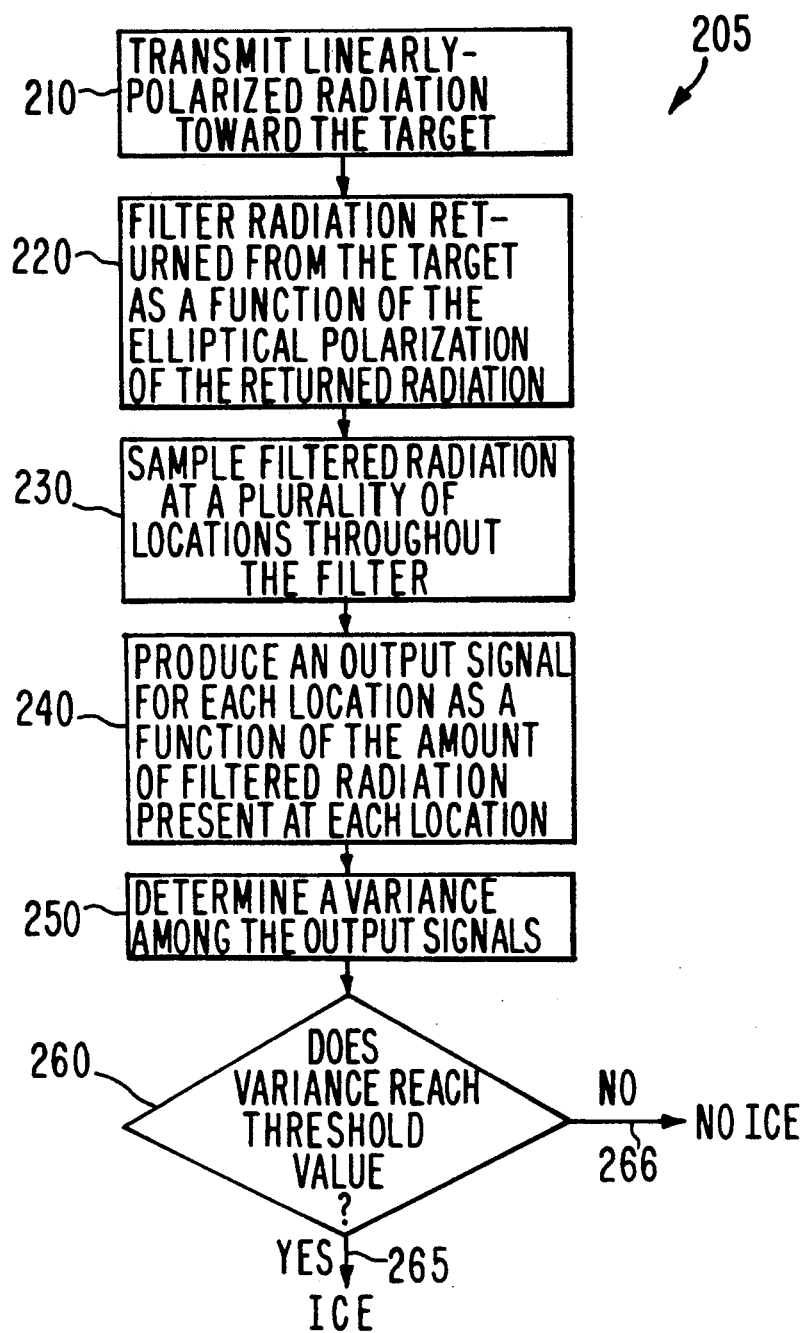
FIG. 5 illustrates a flowchart of a method for ice detection.

FIG. 5 shows a flow diagram of a method 205 for determining the presence or formation of ice. The method is performed by transmitting 210 linearly-polarized radiation toward the target; filtering 220 the radiation returned from the target as a function of the elliptical polarization of the returned radiation as described above, thus resulting in filtered radiation; sampling 230 the filtered radiation at a plurality of locations throughout the filter; producing 240 an output signal for each location that is a function of the amount of filtered radiation received at each said location; determining 250 a variance among the output signals; and, deciding 260 if the variance reaches a threshold value that would indicate the presence of ice on the surface. Ice is declared to be present if the variance reaches a threshold value 265, while ice is declared not to be present if the variance does not reach a threshold value 266. Among other uses, the variance 250 and the outputs 265 and 266 can be stored in a memory means for reference, visually displayed, or used to change the state of an instrument or device.

Figure 6:
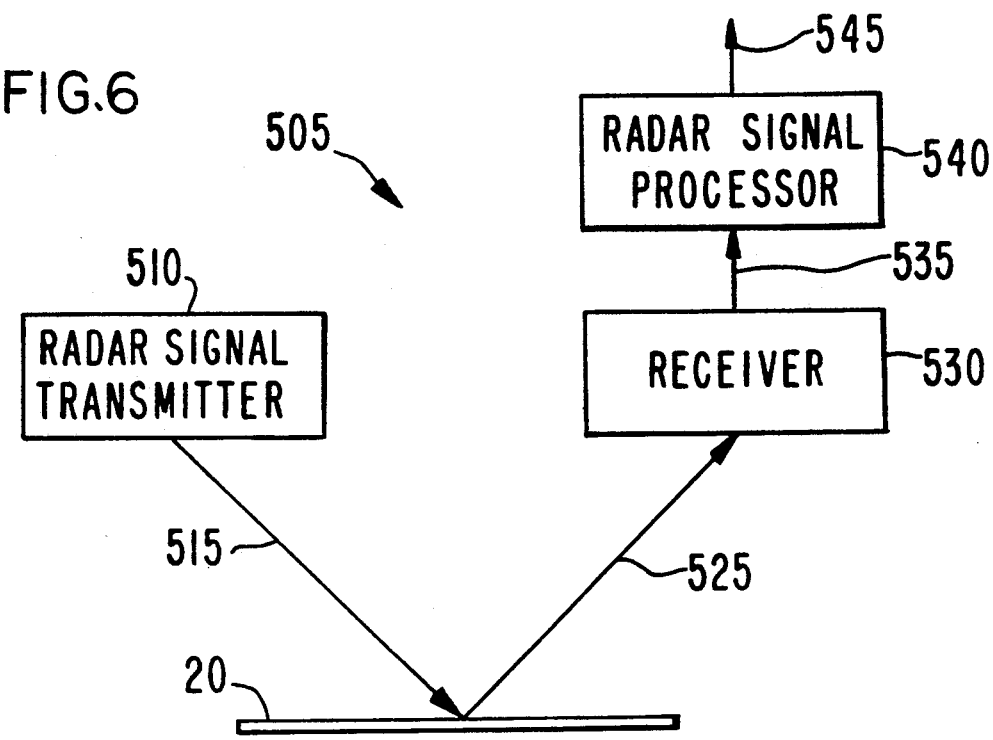
FIG. 6 illustrates one embodiment of a means to measure the thickness of ice.

FIG. 6 illustrates an embodiment of a means to detect the thickness of ice at any given point on the target surface 20. The means 505 for measuring the thickness comprises: a radar transmitter 510 for transmitting a radar signal 515 toward the target 20; a receiver 530 for retrieving the radar signal returned 525 from the target 20 and for producing an output signal 535; and, a radar signal processor 540 for calculating the thickness of the ice as a function of the travel time from sending to receiving the radar signal, an ice-to-air interface dielectric discontinuity, an ice-to-surface interface dielectric discontinuity, and a dielectric constant of the ice. The means for measuring the thickness of ice can operate independently from the ice detection apparatus.

Although theoretically elegant optical solutions could be considered, they are not practical because of the uncertainty about the actual radiation path traversed through the ice segment by the detected return signal 525 and because such solutions would have to assume that the return radiation signal 525 was not a result of the scattering discussed in the ice detection invention above. Other viable options for measuring the ice accumulation are those which depend on verifiable and discernible changes experienced by a propagating signal in ice. For example, the changes in the propagating velocity of an ultrasonic signal traveling through ice.

Figure 7:
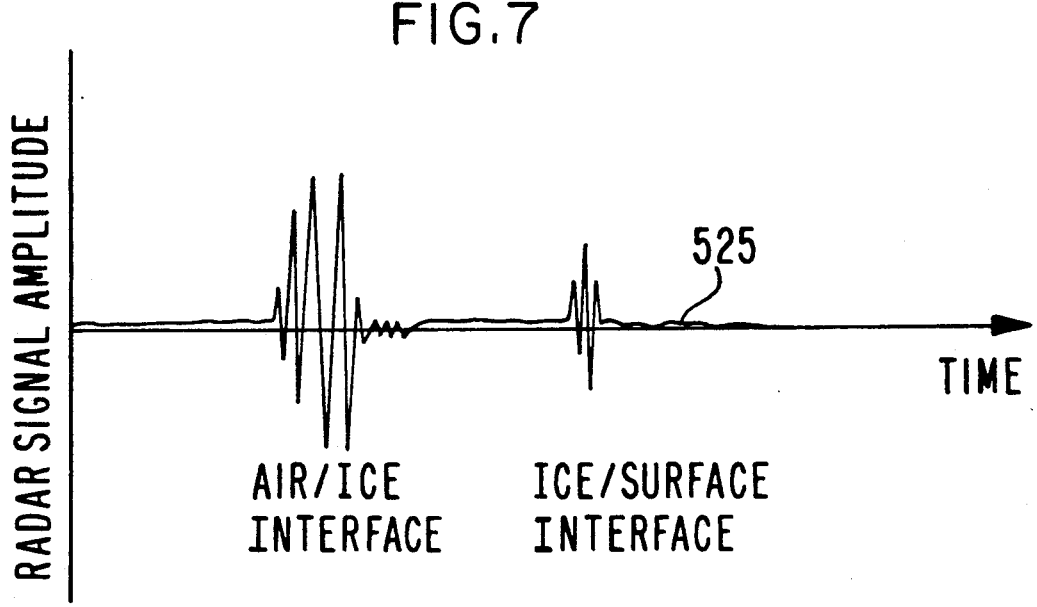
FIG. 7 illustrates an example of a received radar pulse.

Preferably, a short-pulse radar signal 515 from a radar transmitter 510 is directed toward the target 20. A unique pattern in the reflected radar signal occurs because of the differences in the complex dielectric constants of the ice and the surface of the target 20. There is also a similar dielectric discontinuity at the air/ice interface. The reflected radar signal 525 indicates the changing signal levels with respect to time. This change in signal levels reveals two distinct amplitude levels indicative of the delayed reflections at both the ice/surface and air/ice interface. FIG. 7 shows an example of a reflected radar signal.

The returned pulse 525 is received by receiver 530. The receiver 530 may be any standard device capable of detecting a radar signal. The receiver 530 produces an output signal 535 that is a function of the amplitude of the returned pulse 525 received over time. The output signal 535 could be a voltage potential, or an optical, digital, analog, acoustic or other appropriate signal.

The output signal 535 is connected to a radar signal processor 540. The radar signal processor 540 may be any standard voltage amplitude detection system, a digital computer, or similar processing devices. The thickness of the ice is a function of the travel time, t, of the pulse from transmission to receiving, an ice-to-air interface dielectric discontinuity, an ice-to-surface interface dielectric discontinuity, and a dielectric constant of the ice. The thickness, $T_i$, is computed from, $$T_i = 14.99t/(E_{ice})^{\frac{1}{2}},$$

where $E_{ice}$ is the dielectric constant of the ice. Among other uses, the output of the radar signal processor 545 can be stored in a memory means for reference, visually displayed, or used to change the state of an instrument or device.

Because the thickness of ice may be very small, and the half-wavelength of the signal determines the natural threshold below which smaller thicknesses of ice cannot be sensibly discerned, there may be some limitations in the use of a radar signal. Initial observations show an overall limiting detection thickness of about 3.75 mm, below which the radar's resolution may be inadequate.

FIG. 8 shows a flow diagram of a method 305 for determining the thickness of ice. This method can be carried out by: transmitting 310 a radar signal toward a target; retrieving 320 a returned radar pulse; determining 330 a travel time of the radar pulse from transmission to retrieval; and, determining 340 a thickness of the ice on the target as a function of the travel time, an ice-to-air interface dielectric discontinuity, an ice-tosurface interface dielectric discontinuity, and a dielectric constant of the ice. Thus, producing an output 345.

Although the invention has been described with reference to preferred embodiments, the scope of the invention should not be construed to be so limited. Many modifications may be made by those skilled in the art with the benefit of this disclosure without departing from the spirit of the invention. Therefore, the invention should not be limited by the specific examples used to illustrate it, but only be the scope of the appended claims.

What is claimed is:

1. An apparatus for detecting the presence of ice on a target, said apparatus comprising:
   a transmitter for transmitting linearly-polarized radiation toward the target;
   a filter for filtering said radiation returned from the target, wherein the filter outputs filtered radiation that is a function of the elliptical polarization of said returned radiation;
   a sensor for receiving the filtered radiation, comprising a plurality of elemental sensors that each produce an output signal that is a function of the filtered radiation received by the elemental sensor; and,
   coupled to the sensor, a signal processor for determining the variance among the output signals, wherein the signal processor declares the presence of ice when the variance reaches a threshold value.

2. The apparatus of claim 1 wherein the filter comprises:
   a first polarizing filter disposed in the path of said returned radiation,
      wherein the first polarizing filter outputs semi-filtered radiation that is a function of the elliptical polarization of said returned radiation; and,
   disposed in the path of the semi-filtered radiation, a second polarizing filter, rotatable with respect to the first polarizing filter and disposed in a plane parallel therewith,
      wherein the second polarizing filter outputs filtered radiation as a function of the elliptical polarization of the radiation received.

3. The apparatus of claim 1 further comprising:
   means for measuring the thickness of detected ice, wherein said means for measuring the thickness of ice comprises:

a radar transmitter for transmitting a radar signal toward the target;
   a receiver for retrieving said radar signal returned from the target; and,
   coupled to said retriever, a radar signal processor for gauging a thickness of the ice as a function of a travel time of the radar signal from the time of transmission by the transmitter to the time of retrieval by the retriever, an ice-to-air interface dielectric discontinuity, an ice-to-surface interface dielectric discontinuity, and a dielectric constant of the ice.

4. The apparatus of claim 1 wherein said returned radiation is reflected from the target.

5. The apparatus of claim 1 wherein said returned radiation is refracted by the target.

6. The apparatus of claim 1 wherein said target is an aircraft.

7. The apparatus of claim 1 wherein said target is a surface for travel.

8. A method for detecting ice on a target, said method comprising the steps of:
   transmitting linearly-polarized radiation toward the target;
   filtering the radiation returned from the target to produce filtered radiation that is a function of the elliptical polarization of the returned radiation;
   sampling the filtered radiation at a plurality of locations throughout the filter;
   producing an output signal for each location, wherein each output signal is a function of the amount of filtered radiation present at each said location; and,
   determining a variance among said output signals, wherein ice is declared to be present if the variance reaches a threshold value.

9. The method of claim 8, further comprising the additional steps of:
   transmitting a radar signal toward the target;
   retrieving a returned radar pulse;
   determining a travel time of the radar pulse from a transmitting time to a retrieving time; and,
   determining a thickness of the ice on the target;
   wherein the thickness of the ice is a function of the travel time, an ice-to-air interface dielectric discontinuity, an ice-to-surface interface dielectric discontinuity, and a dielectric constant of the ice.

* * * * *